United States Patent
Hörnig

(10) Patent No.: US 7,736,055 B2
(45) Date of Patent: Jun. 15, 2010

(54) X-RAY DEVICE

(75) Inventor: Mathias Hörnig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 131 days.

(21) Appl. No.: 11/817,743

(22) PCT Filed: Mar. 6, 2006

(86) PCT No.: PCT/EP2006/060469

§ 371 (c)(1),
(2), (4) Date: Sep. 4, 2007

(87) PCT Pub. No.: WO2006/094955

PCT Pub. Date: Sep. 14, 2006

(65) Prior Publication Data

US 2008/0165933 A1    Jul. 10, 2008

(30) Foreign Application Priority Data

Mar. 8, 2005    (DE) ................. 10 2005 010 659

(51) Int. Cl.
*A61B 6/08* (2006.01)
(52) U.S. Cl. .................................... 378/206
(58) Field of Classification Search .......... 378/205–207
See application file for complete search history.

(56) References Cited

U.S. PATENT DOCUMENTS

| | | | |
|---|---|---|---|
| 4,065,211 A * | 12/1977 | Vig | 356/139.07 |
| 4,087,694 A | 5/1978 | Hellstrom et al. | 378/195 |
| 4,092,544 A | 5/1978 | Grim | 250/491 |
| 5,241,578 A * | 8/1993 | MacMahon | 378/154 |
| 5,517,546 A * | 5/1996 | Schmidt | 378/206 |
| 6,227,704 B1 | 5/2001 | Bani-Hashemi et al. | 378/206 |
| 6,435,715 B1 | 8/2002 | Betz et al. | 378/4 |
| 6,447,164 B1 | 9/2002 | Polkus | 378/206 |
| 2003/0194056 A1 | 10/2003 | Spahn | 378/205 |
| 2005/0058256 A1 | 3/2005 | Beimler et al. | 378/162 |

FOREIGN PATENT DOCUMENTS

| | | |
|---|---|---|
| DE | 4435112 | 9/1994 |
| DE | 10118183 | 11/2002 |
| DE | 10341541 | 4/2005 |

OTHER PUBLICATIONS

Search Report and Written Opinion for Application No. PCT/EP2006/060469 (11 pages), May 30, 2006.

\* cited by examiner

*Primary Examiner*—Irakli Kiknadze
(74) *Attorney, Agent, or Firm*—King & Spalding L.L.P.

(57) ABSTRACT

In order to achieve a consistently good image quality, an X-ray device has an X-ray source in the form of an X-ray radiator (1) and an X-ray detector (2) with a precisely defined mutual arrangement, and a subsystem (5-7; 10-11) for detecting any deviation between the actual mutual arrangement and the precise mutual arrangement of X-ray source and X-ray detector (2). Optical detection of deviations is preferably provided.

13 Claims, 2 Drawing Sheets

X-RAY DEVICE

CROSS-REFERENCE TO RELATED APPLICATIONS

This application is a U.S. national stage application of International Application No. PCT/EP2006/060469 filed Mar. 6, 2006, which designates the United States of America, and claims priority to German application number 10 2005 010 659.5 filed Mar. 8, 2005, the contents of which are hereby incorporated by reference in their entirety.

TECHNICAL FIELD

The invention relates to an X-ray apparatus having an X-ray source and an X-ray detector.

BACKGROUND

In the case of X-ray apparatuses such as these, it is critically important that an X-ray source and an X-ray detector, in particular a digital X-ray detector, are arranged as exactly as possible relative to one another, in order to ensure the same high image quality all the time. Inter alia, the exact relative arrangement ensures uniformly centered illumination of the X-ray detector by an X-ray beam produced by the X-ray source, uniform dosage distribution of the X-ray beam on the X-ray detector, dazzle control that is symmetrical with respect to the X-ray detector, and alignment, accurately centered with respect to a focus of the X-ray source, of a scattered beam grid attached to the X-ray detector. In general, in an X-ray system, after installation at its intended location, the X-ray emitter and the X-ray detector are aligned relative to one another once such that any discrepancies in the instantaneous relative arrangement from an exact relative arrangement are within a tolerance value defined for the X-ray apparatus. This situation is referred to in the following text as the necessary relative arrangement.

Over the course of time, loss of adjustment can occur in an X-ray apparatus, leading to the discrepancy in the positioning of the X-ray emitter relative to the X-ray detector going considerably beyond the tolerance values, with the image quality deteriorating as a result of this. Furthermore, even in applications which require major tilting of the X-ray emitter and of the X-ray detector, it is possible for mechanical holders such as telescopic holders to be severely loaded by the masses of the components, such that the permissible tolerance values for the discrepancies are exceeded.

So-called "locating pins" are known for X-ray detectors, pins which are attached directly to the a-Si or a-Se plate of the X-ray detector, which can be aligned by means of matching holes incorporated in a holder for the X-ray detector so as to prevent any major discrepancy from the original position. Furthermore, X-ray apparatuses are also known in which the X-ray detector is held in its position by means of a spring mechanism.

SUMMARY

An X-ray apparatus may have a constantly good image quality according to an embodiment of an X-ray apparatus which comprises an X-ray source and an X-ray detector, for which an exact relative arrangement with respect to one another is defined, and an associated subsystem for detection of any discrepancy between an instantaneous relative arrangement and the exact relative arrangement between the X-ray source and the X-ray detector.

According to an enhancement, the subsystem can be physically integrated in the X-ray apparatus. According to a further enhancement, a first part of the subsystem can be arranged adjacent to the X-ray source or its housing, and a second part of the subsystem can be arranged adjacent to the X-ray detector or its housing. According to a further enhancement, the subsystem may have optical detection for detection of any discrepancy from the exact relative arrangement. According to a further enhancement, the subsystem may have at least one light source, at least one light detector and at least one light reflector. According to a further enhancement, the light reflector can be arranged adjacent to the X-ray detector or its housing, and the light source and the light detector can be arranged adjacent to the X-ray source or its housing. According to another enhancement, the light reflector can be arranged adjacent to the X-ray source or its housing, and the light source and the light detector can be arranged adjacent to the X-ray detector or its housing. According to a further enhancement, at least one light beam is transmitted by the light source, the at least one light beam is reflected on the light reflector, and the at least one reflected light beam, in particular its intensity, is detected by the light detector. According to a further enhancement, a change in the intensity of the reflected light beam can be provided as a measure of any discrepancy in the exact relative arrangement between the X-ray detector and the X-ray source. According to a further enhancement, any adjustment that needs to be carried out can be monitored by the subsystem in order to correct for any discrepancy from the exact relative arrangement. According to a further enhancement, a laser can be provided as the light source. According to a further enhancement, a photodetector can be provided as the light detector. According to a further enhancement, the X-ray apparatus can be in the form of an irradiation and/or radiography X-ray apparatus.

BRIEF DESCRIPTION OF THE DRAWINGS

The invention as well as further advantageous refinements will be explained in more detail in the following text with reference to schematically illustrated exemplary embodiments in the drawing, without this implying any restriction of the invention to these exemplary embodiments. In the figures.

DETAILED DESCRIPTION

In the X-ray system according to various embodiments, a constantly high image quality can be achieved in that the associated subsystem is used to reliably detect any discrepancy from an exact relative arrangement between the X-ray emitter and the X-ray detector immediately after it occurs, thus making it possible to initiate steps for readjustment in order to correct for the discrepancy between the instantaneous and the exact relative arrangement; readjustment is necessary when the discrepancy in the instantaneous relative arrangement from the relative arrangement that is defined as being exact exceeds permissible tolerance values. In particular, a constantly good image quality is obtained in that, uniformly centered illumination of the X-ray detector by the X-ray beam, uniform dosage distribution of the X-ray beam on the X-ray detector, dazzle control that is symmetrical with respect to the X-ray detector, and accurate alignment of a scattered beam grid are possible while maintaining the necessary relative arrangement between the X-ray source and the X-ray detector.

According to an embodiment, the subsystem for detection of any discrepancy between the instantaneous relative arrangement and the exact relative arrangement has optical detection. For particularly low-cost and nevertheless accurate detection, the subsystem advantageously has at least one light source, at least one light detector and at least one light reflector.

According to a further embodiment, the light reflector is arranged adjacent to the X-ray detector or its housing, and the light source and the light detector are arranged adjacent to the X-ray source or its housing; the physical proximity between the subsystem and the X-ray detector and X-ray source allows particularly precise detection. Provision is advantageously made for transmission of at least one light beam by the light source, reflection of the at least one light beam on the light reflector, and detection of the at least one reflected light beam, in particular its intensity, by the light detector.

According to a further embodiment, a change in the intensity of the reflected light beam is provided as a measure of any discrepancy between the instantaneous relative arrangement and the exact relative arrangement between the X-ray detector and the X-ray source.

According to a further embodiment, an X-ray apparatus in particular in the form of an irradiation and/or radiography X-ray apparatus can be provided.

Figure 1:
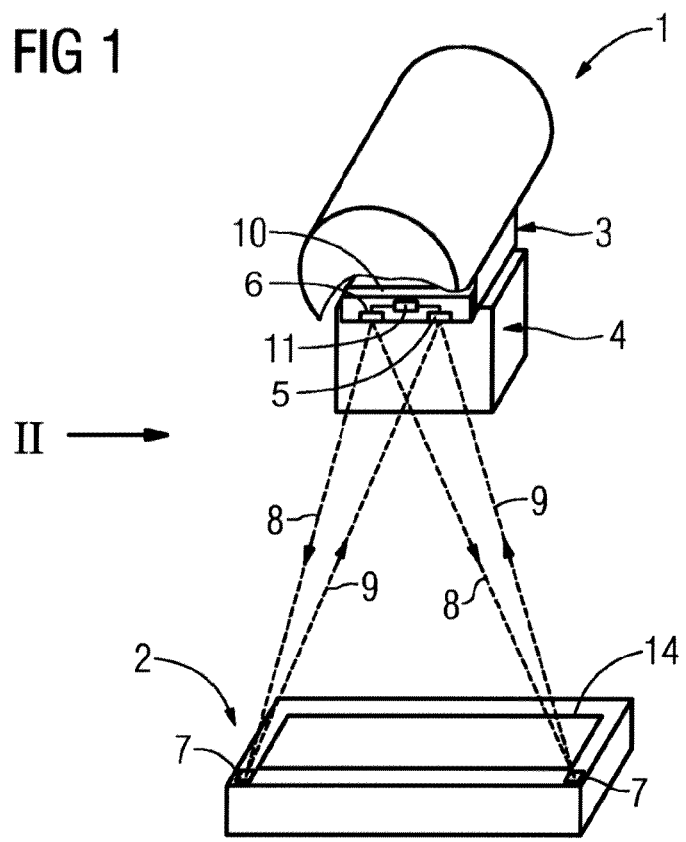
FIG. 1 shows a perspective view of an X-ray detector and an X-ray emitter in a relative arrangement with a subsystem according to an embodiment in which the light reflector is arranged adjacent to the X-ray detector or its housing, and the light source and the light detector are arranged adjacent to the X-ray source or its housing, for detection of any discrepancy between the instantaneous and the required relative arrangement.
Figure 2:
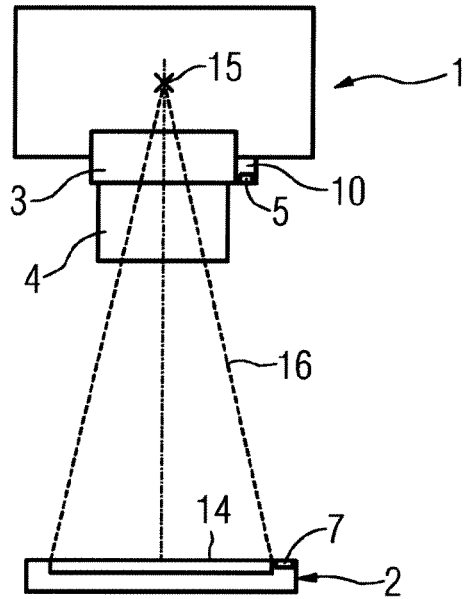
FIG. 2 shows a side view of the X-ray emitter shown in FIG. 2, with a first part of the subsystem attached to the emitter housing.
Figure 3:
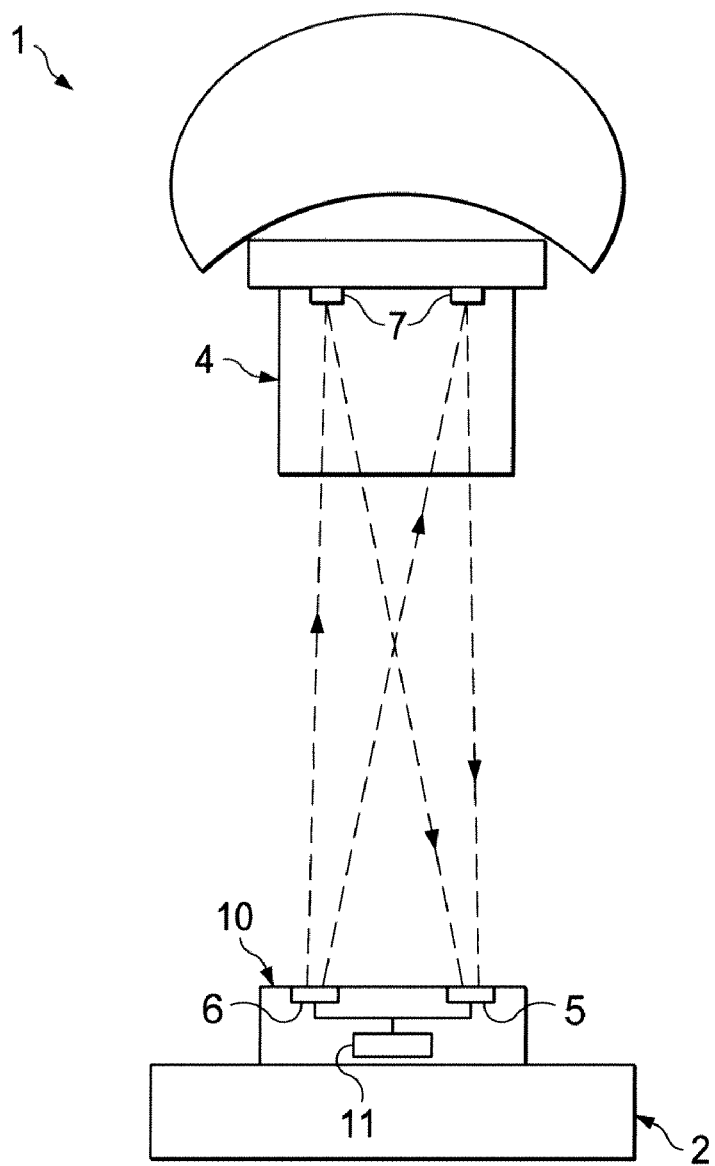
FIG. 3 shows a perspective view of X-ray detector and an X-ray emitter in a relative arrangement with a subsystem according to an embodiment in which the light reflector is arranged adjacent to the X-ray source or its housing, and the light source and the light detector are arranged adjacent to the X-ray detector or its housing, for the detection of any discrepancy between the instantaneous and the required relative arrangement.

FIG. 1 and FIG. 2 respectively show a perspective view and a side view as parts of an X-ray apparatus of an X-ray source in the form of an X-ray emitter 1 with an emitter flange 3 and a collimator 4, as well as a preferably digital X-ray detector 2. The X-ray emitter 1 and X-ray detector 2 have an exact relative arrangement with respect to one another, which can normally be set when the X-ray apparatus is initially installed. As indicated in FIG. 2, the expression an exact relative arrangement in general means that a focus 15 of an X-ray beam produced by the X-ray emitter 1 is aligned such that it is precisely centered on an active area 14 of the X-ray detector 2.

If any discrepancies from the exact relative arrangement are within a tolerance value, then this state is referred to as the required relative arrangement. Discrepancies which exceed a tolerance value lead to unfocused, inhomogeneous and thus qualitatively poor X-ray films. By way of example, tolerance values may be in the region of 1 mm with respect to lateral displacement. Discrepancies may occur either gradually or spontaneously, when the X-ray emitter 1 and/or the X-ray detector 2 are/is moved to highly tilted recording positions, in which their holders, for example telescopic arms, are subject to extreme loads by the masses.

A subsystem 5-7; 10-11 according to an embodiment is advantageously physically integrated in the X-ray apparatus. According to one refinement of the invention, a first part 5; 6; 10; 11 of the subsystem 5-7; 10-11 is arranged adjacent to the X-ray emitter 1 or its housing, and a second part 7 of the subsystem 5-7; 10-11 is arranged adjacent to the X-ray detector 2 or its housing. The first part 5; 6; 10; 11 of the subsystem 5-11 contains a light source in the form of a laser 6, a light detector in the form of a photodetector 5, and an evaluation device 11; the laser 6, the photodetector 5 and the evaluation device 11 are jointly arranged in a measurement head 10, adjacent to the emitter flange 3 associated with the housing of the X-ray emitter.

The second part 7 of the subsystem 5-11 contains two light reflectors 7, which are located at two adjacent corners on the X-ray detector 2, away from its active area 14. By way of example, it is also possible to provide four light reflectors 7 at all four corners of the X-ray detector 2. By way of example, small mirrors or other surfaces which at least partially reflect the transmitted light beam 8 from the light source are suitable for use as light reflectors. The position of the first part 5; 6; 10; 11 of the subsystem 5-11 adjacent to the emitter flange 3 close to the focus 15 of the X-ray beam 16 makes it possible to detect particularly simply discrepancies which result from defocusing of the X-ray beam 16 with respect to the X-ray detector 2. By way of example, discrepancies such as these include tilting of the X-ray emitter 1 with respect to the X-ray detector 2.

The laser 6 transmits a preferably convergent light beam 8 to each of the light reflectors 7, with the light reflectors 7 being adjusted such that the reflected light beams 9 arrive precisely centrally at the photodetector 5, when the relative arrangement is exact without any discrepancy, and the intensity of the reflected light beams 9 assumes a maximum value. The intensities are in this case evaluated in the evaluation device 11. The evaluation can also be carried out by a control system which is generally provided for the X-ray apparatus. By way of example, the subsystem 5-7; 10-11 may be adjusted when the X-ray apparatus is initially installed.

In the event of any discrepancy from the exact relative arrangement between the X-ray emitter 1 and the X-ray detector 2, the reflected light beam 9 no longer strikes the photodetector 5 precisely centrally, resulting in a reduction in the intensity, which is detected by means of the evaluation device 11 by comparison with the maximum value. The reduction in the intensity can in consequence be used to deduce that there is a discrepancy between the instantaneous relative arrangement and the exact relative arrangement between the X-ray emitter 1 and the X-ray detector 2.

If the discrepancy and therefore the intensity reduction exceed a previously defined tolerance value, that is to say if the instantaneous relative arrangement is outside the required relative arrangement, then readjustment is necessary. In this case, for example, the evaluation device 11 can pass a signal to an indication on the measurement head, thus informing the user of the need for readjustment. A detection process may be carried out, for example, before each X-ray is recorded, at regular time intervals, or continuously.

According to a further embodiment, the subsystem 5-7; 10-11 carries out a monitoring process for any adjustment that needs to be carried out for correction of the discrepancy from the exact relative arrangement. Readjustment is therefore carried out until the intensity of the reflected light beams 9 once again corresponds to its maximum value, or is at least in a defined tolerance band around the maximum value, that is to say until the instantaneous relative arrangement corresponds to the exact or at least the required relative arrangement.

In summary, in order to ensure constantly good image quality, an X-ray apparatus which has an X-ray source in the form of an X-ray emitter 1, and has an X-ray detector 2, which have an exactly defined relative arrangement with respect to one another, has a subsystem 5-7; 10-11 for detection of any discrepancy between an instantaneous relative arrangement and the exact relative arrangement between the X-ray source and the X-ray detector 2; optical detection is preferably provided for the discrepancy.

The invention claimed is:

1. An X-ray apparatus comprising an X-ray source and an X-ray detector, for which an exact relative arrangement with respect to one another is defined, and an associated subsystem for detection of any discrepancy between an instantaneous relative arrangement and the exact relative arrangement between the X-ray source and the X-ray detector;
   wherein the subsystem provides optical detection of any discrepancy from the exact relative arrangement, the subsystem including at least one light source, at least one light detector and at least one light reflector; and
   wherein the subsystem is configured in one of (a) a first configuration in which the at least one light reflector is arranged adjacent to the X-ray detector or its housing, and the at least one light source and the at least one light detector are arranged adjacent to the X-ray source or its housing or (b) a second configuration in which the at least one light reflector is arranged adjacent to the X-ray detector or its housing, and the at least one light source and the at least one light detector are arranged adjacent to the X-ray source or its housing.

2. The X-ray apparatus according to claim 1, wherein the subsystem is physically integrated in the X-ray apparatus.

3. The X-ray apparatus according to claim 1, wherein at least one light beam is transmitted by the at least one light source, the at least one light beam is reflected on the at least one light reflector, and the at least one reflected light beam, in particular its intensity, is detected by the at least one light detector.

4. The X-ray apparatus according to claim 3, wherein a change in the intensity of the at least one reflected light beam is provided as a measure of any discrepancy in the exact relative arrangement between the X-ray detector and the X-ray source.

5. The X-ray apparatus according to claim 1, wherein the subsystem monitors for adjustments needed in order to correct for any discrepancy from the exact relative arrangement.

6. The X-ray apparatus according to claim 1, wherein the at least one light source comprises at least one laser.

7. The X-ray apparatus according to claim 1, wherein the at least one light detector comprises at least one photodetector.

8. The X-ray apparatus according to claim 1, which is in the form of an irradiation and/or radiography X-ray apparatus.

9. The X-ray apparatus according to claim 1, wherein at least one light beam is transmitted by the at least one light source, the at least one light beam is reflected on the at least one light reflector, and the at least one reflected light beam, in particular its intensity, is detected by the at least one light detector.

10. The X-ray apparatus according to claim 9, wherein a change in the intensity of the at least one reflected light beam is provided as a measure of any discrepancy in the exact relative arrangement between the X-ray detector and the X-ray source.

11. An X-ray apparatus comprising an X-ray source and an X-ray detector, for which an exact relative arrangement with respect to one another is defined, and an associated subsystem for detection of any discrepancy between an instantaneous relative arrangment and the exact relative arrangement between the X-ray source and the X-ray detector,
    wherein the subsystem is physically integrated in the X-ray apparatus,
    wherein the subsystem has optical detection for detection of any discrepancy from the exact relative arrangement, and wherein the subsystem has at least one light source, at least one light detector and at least one light reflector, and
    wherein the subsystem is configured in one of (a) a first configuration in which the at least one light reflector is arranged adjacent to the X-ray detector or its housing, and the at least one light source and the at least one light detector are arranged adjacent to the X-ray source or its housing or (b) a second configuration in which the at least one light reflector is arranged adjacent to the X-ray detector or its housing, and the at least one light source and the at least one light detector are arranged adjacent to the X-ray source or its housing.

12. The X-ray apparatus according to claim 11, wherein at least one light beam is transmitted by the at least one light source, the at least one light beam is reflected on the at least one light reflector, and the at least one reflected light beam, in particular its intensity, is detected by the at least one light detector.

13. The X-ray apparatus according to claim 12, wherein a change in the intensity of the at least one reflected light beam is provided as a measure of any discrepancy in the exact relative arrangement between the X-ray detector and the X-ray source.

* * * * *